United States Patent [19]

Yurchak

[11] Patent Number: 4,814,536
[45] Date of Patent: Mar. 21, 1989

[54] CONVERSION OF OXYGENATES TO GASOLINE AT VARIABLE SPACE VELOCITY

[75] Inventor: Sergei Yurchak, Media, Pa.

[73] Assignee: Mobil Oil Corporation, New York, N.Y.

[21] Appl. No.: 133,416

[22] Filed: Dec. 15, 1987

[51] Int. Cl.[4] ............................................. C07C 11/20
[52] U.S. Cl. .................................. 585/408; 585/640; 585/733
[58] Field of Search ....................... 585/408, 640, 733

[56] References Cited

U.S. PATENT DOCUMENTS

| | | | |
|---|---|---|---|
| 3,931,349 | 1/1976 | Kuo | 260/668 |
| 3,998,899 | 12/1976 | Daviduk et al. | 260/668 |
| 4,044,061 | 8/1977 | Chang et al. | 260/668 |
| 4,404,414 | 9/1983 | Penick et al. | 585/469 |
| 4,423,272 | 12/1983 | Forbus et al. | 502/53 |

Primary Examiner—Curtis R. Davis
Attorney, Agent, or Firm—Alexander J. McKillop; Charles J. Speciale; L. G. Wise

[57] ABSTRACT

An improved MTG process for converting lower aliphatic $C_1$-$C_4$ oxygenates, such as methanol, to gasoline boiling range hydrocarbons is disclosed which is capable of obtaining improved cycle average gasoline yields and improved catalyst life by programming the methanol WHSV from high values at essentially quantitative methanol conversion at the start of a cycle to low values at essentially quantitative methanol conversion at the end of a cycle.

17 Claims, 3 Drawing Sheets

CONVERSION OF OXYGENATES TO GASOLINE AT VARIABLE SPACE VELOCITY

FIELD OF THE INVENTION

The present invention relates to the production of synthetic gasoline. The present invention particularly relates to a process for converting lower aliphatic $C_1$-$C_4$ oxygenates, such as methanol, to gasoline. More particularly, the present invention relates to the conversion of oxygenates to gasoline in high yield under varying rates of oxygenates weight hourly space velocity (WHSV).

BACKGROUND OF THE INVENTION

Processes for converting lower alcohols such as methanol to hydrocarbons are known and have become of great interest in recent times because they offer an attractive way of producing liquid hydrocarbon fuels, especially gasoline, from sources which are not of liquid petroliferous origin. In particular, they provide a way by which methanol can be converted to gasoline boiling range products in good yields. The methanol, in turn, may be readily obtained from coal by gasification to synthesis gas and conversion of the synthesis gas to methanol by well-established industrial processes. As an alternative, the methanol may be obtained from natural gas by other conventional processes.

The conversion of methanol to hydrocarbon products may take place in a fluidized bed process as described, for example, in U.S. Pat. Nos. 4,071,573 and 4,138,440, or in a fixed bed as described in U.S. Pat. Nos. 3,998,899, 3,931,349 and 4,035,430. In the fixed bed process, the methanol is usually first subjected to a dehydrating step, using a catalyst such as gamma-alumina, to form an equilibrium mixture of methanol, dimethyl ether (DME) and water. This mixture is then passed over a catalyst such as zeolite ZSM-5 which brings about the conversion to the hydrocarbon products which are mainly in the range of light gas to gasoline. The water may be removed from the methanol dehydration products prior to conversion to hydrocarbons as may the methanol which can be recycled to the dehydration step, as described in U.S. Pat. No. 4,035,430. Removal of the water is desirable because the catalyst may tend to become deactivated by the presence of the water vapor at the reaction temperatures employed, but this step is by no means essential.

The conversion of oxygenates, or more particularly methanol, to gasoline, typically referred to as the MTG process, is highly energy efficient. The hydrocarbons from the conversion contain 95 percent of the energy in the original methanol feed; the other five percent is released as exothermic heat and used during the conversion reaction. Recycling of process gas limits the temperature rise across the fixed catalyst bed to less than 95° C. Also during the reaction, a small amount of hydrocarbon is deposited on the catalyst as coke, requiring periodic catalyst regeneration. Operation of the process, however, is continuous because additional reactors, arranged in parallel, permit an individual reactor to swing from operation to regeneration while another goes from regeneration to operation. The final gasoline yield from the fixed bed process, after alkylating the light olfins formed, is about 85–90 percent by weight of the total hydrocarbons formed. The remaining hydrocarbons are available mostly as liquid petroleum gas (LPG) and a small amount of fuel gas.

The conversion of oxygenates is described in depth by C. D. Chang, Catal. Rev.-Sci. Eng., 25, 1(1983) and in U.S. Pat. Nos. 3,931,349 to Kuo and 4,404,414 to Penick et al. These references are incorporated herein in their entirety.

Major problems facing research workers in the field of the MTG process include improvements in cycle average yield of gasoline and the extension of catalyst cycle life. Improvements in yield and catalyst life are known to be inextricably related, whereby advances in one problem area are typically achieved at the expense of the other. Process improvements leading to the common enhancement of gasoline yield and catalyst life have been most elusive. One factor that complicates the effort of research workers to achieve the desired advances in yield and catalyst cycle life is the requirement that the MTG process operate at or near quantitative methanol conversion. Less than quantitative conversions, or "methanol breakthrough," presents severe problems in waste disposal and/or methanol recovery which quickly leads to punishing economic penalties and, therefore, is to be avoided. Accordingly, whatever advances research workers are to make in yield and catalyst life for MTG improvements must be made while maintaining essentially quantitative conversion of methanol.

Therefore, one object of the present invention is to significantly improve the cycle average gasoline yield in the MTG process at essentially quantitative methanol conversion. Another object of the present invention is to significantly improve the life of the conversion catalyst in the MTG process.

A further object of the present invention is to improve the MTG process from an economical standpoint by improving cycle average gasoline yields while increasing the useful life of the conversion catalyst, at essentially quantitative methanol conversion.

SUMMARY OF THE INVENTION

It has been discovered that the foregoing objectives of the present invention are accomplished in the MTG process by operating the conversion step from methanol, or methanol equivalents such as hydrocarbon oxygenates, to gasoline under a variable feedstock feedrate WHSV based on the catalyst charge. The WHSV is programmed to decline from an initial high value at the start of the cycle to a lower value of the end of the cycle in a manner and in an amount just sufficient to maintain the conversion of methanol at or near quantitative. When operated in accordance with the foregoing description, the MTG gasoline cycle average yield is increased in comparison to MTG operation as described in the prior art. Further, the effective life of the conversion catalyst, i.e., cycle length, as measured by the time interval or feed stock processed between catalyst regeneration, is increased.

Accordingly, for a cyclic process for converting lower aliphatic oxygenated hydrocarbon feedstock to aromatics-rich gasoline range hydrocarbons the process comprises the steps of; contacting the feedstock with a fixed bed of acid shape selective medium pore zeolite conversion catalyst particles at elevated temperature under conversion conditions;

maintaining feedstock initial feed rate at high weight hourly space velocity in the presence of fresh acid catalyst having high acid activity;

decreasing the feedstock feed rate space velocity with decreasing acid catalyst activity during cycle progression; and interrupting feedstock conversion at a predetermined low catalyst activity for periodic catalyst regeneration to increase catalyst activity.

DETAILED DESCRIPTION OF THE INVENTION

Starting Materials

Figure 1:
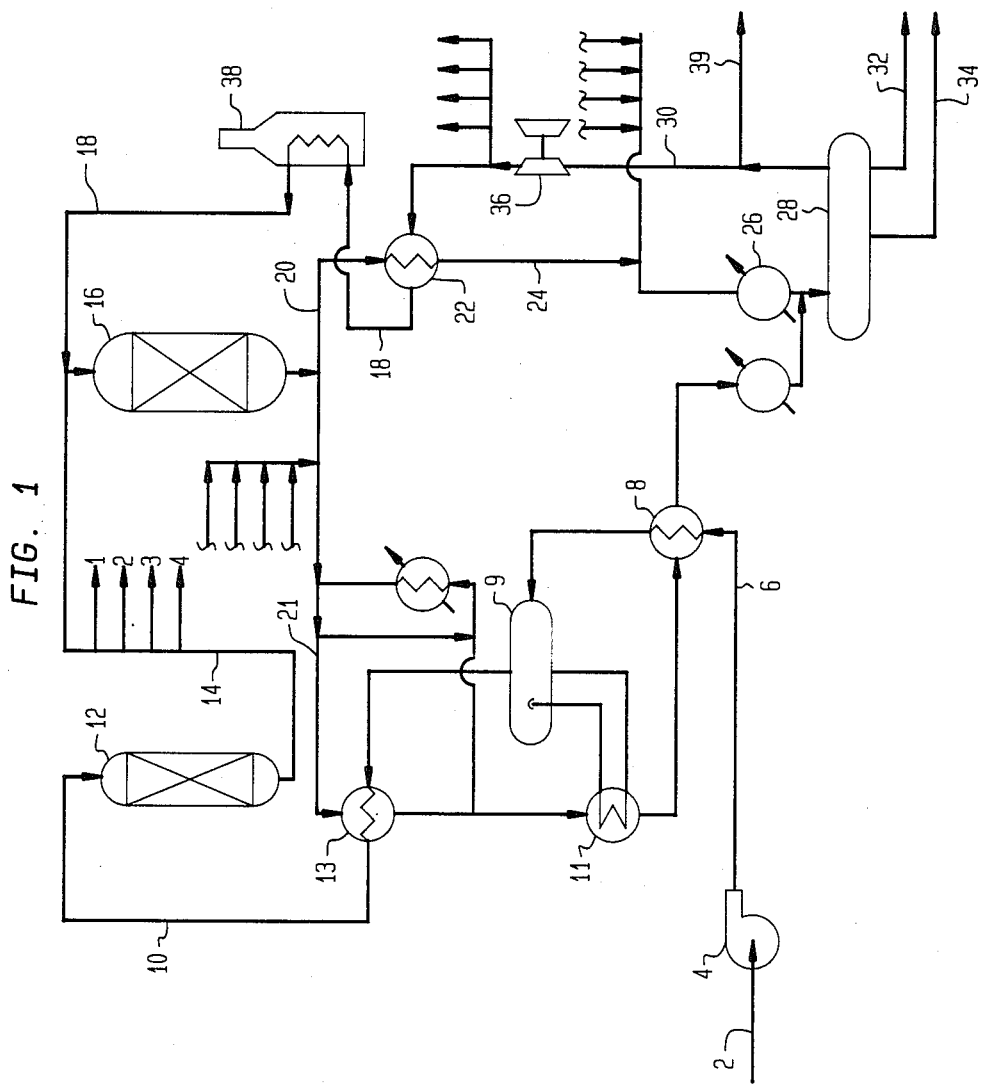
FIG. 1 is a schematic process flow arrangement for converting methanol in two separate sequentially arranged fixed catalyst beds for the typical MTG process.

The present process is useful for the conversion of a number of differing oxygenated organic compounds into hydrocarbon products. The process is useful for the conversion of aliphatic compounds including lower alcohols such as methanol, ethanol and propanol, ethers such as DME and diethyl ether, ketones such as acetone and methyl ethyl ketone, aldehydes such as acetaldehyde, esters such as methyl formate, methyl acetate and ethyl acetate, carboxylic acids such as acetic acid, butyric acid and their anhydrides e.g., acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions. The product in each case will be a hydrocarbon mixture ranging from light gas to heavier fractions ($C_{10+}$) but will generally be concentrated in the gasoline boiling range ($C_5$-220° C.). The process is particularly useful in the catalytic conversion of methanol to hydrocarbons in the gasoline boiling range and, for convenience, the process will be described below with reference to such a process although it should be remembered that the principles are applicable to a broader range of conversion, as set out above.

If methanol is used as the starting material for the process it is preferred to subject it to an initial dehydration step to form an intermediate product comprising dimethyl ether (DME). The DME is then passed to the hydrocarbon step with either complete, partial or no separation of the unreacted methanol and the water produced as a by-product of the dehydration. However, it is not essential to carry out this dehydration even though it is preferred. It is possible to dehydrate only part of the methanol with, for example, the dehydration product going to one reactor and the raw methanol going to another.

Because the oxygenated charge may be fed into the reactors in different forms, e.g., methanol and DME, it will often be convenient, for purposes of calculating recycle ratio and other factors, to base the calculations upon a single equivalent charge. For example, if both methanol and DME are fed to the reactors, the total charge may be reduced to a basis of "methanol equivalents" in which one mole of DME is equal to two methanol equivalents. Thus, the reactant flow at any point may be readily reduced to a single value from which other may be derived, e.g., recycle ratio, or reactant or feedstock feedrate expressed as weight hourly space velocity (WHSV) based on catalyst.

Process Outline

The conversion of methanol or methanol equivalents to gasoline is accomplished in contact with zeolite catalysts, such as Z5M-5, usually quantitatively in the presence of active catalyst. In addition to gasoline and other hydrocarbons, water is a reaction by-product. However, process variables must be carefully managed because the conversion of methanol to gasoline boiling components is a highly exothermic reaction releasing approximately 750 BTU of heat per pound of methanol. This amount of heat release will result in an adiabatic temperature increase of about 1200 degrees F. for pure methanol feed. In an adiabatic catalyst bed reactor, this large temperature increase will result in high catalyst aging rates, and possibly cause thermal damage to the catalyst. Furthermore, such high temperatures could cause an undesirable product distribution to be obtained. Therefore, it is critical to the conversion of methanol to useful products to provide sufficient heat removing or dissipating facilities particularly during initial contact with the crystalline zeolite conversion catalyst so that the maximum temperature encountered in any portion of the zeolite catalyst conversion step is below an upper predetermined limit.

The exothermic character of the conversion reaction also requires careful management of the methanol feedrate in terms of weight hourly space velocity (WHSV) based on catalyst loading. "Methanol breakthrough," a term of art indicating the appearance of methanol in the aqueous product stream and, therefore, less than quantitative conversion, has generally been followed to signal the end of the process cycle and the need to regenerate catalyst. The production of even very dilute aqueous methanol product streams presents an operator with very costly waste disposal or separation problems and must be avoided. Accordingly, when any combination of process parameters produce a methanol conversion of less than 99%, or more typically 99.9%, the cycle under those conditions is ended largely for economic reasons. Of course, if disposal or recovery of unconverted methanol is not a consideration, the cycle can be continued to less than 99% methanol conversion.

Referring now to FIG. 1 a typical process flow diagram of the MTG process is presented. Crude methanol in a liquid phase condition is charged to the process by conduit 2 communicating with pump 4. The methanol is pressured to about 2500 kPa (350 psig) in pump 4 and then passed by conduit 6 to heat exchanger 8 wherein the liquid methanol is preheated. It is then passed into drum 9 where it is vaporized at about 185° C. (400° F.) by indirect heat exchanger 11. The methanol is then superheated in indirect exchanger 13 to about 315° C. (600° F.) and it is passed by conduit 10 to the inlet of the dimethyl ether forming catalytic reactor 12. In catalyst contained in reactor 12, a fixed bed of gamma alumina catalyst is maintained as a fixed bed of catalyst through which the methanol reactant passed downwardly through or as an annular bed of catalyst for radial flow of reactant material therethrough. A single down-flow fixed catalyst bed or a plurality of separate fixed down-flow catalyst beds are arranged for converting the methanol feed under restricted temperature conditions as herein described to essentially an equilibrium product comprising methanol, dimethyl ether and water at a temperature of about 395°-415° C. (740°-780°F.) due to the exothermic temperature rise catalytically generated in the operation. The equilibrium product thus obtained may be construed as an ether rich product which is then passed by conduit 14 to a second reactor stage 16 housing one or more separate parallel or sequentially arranged beds of a ZSM-5 type of crystalline zeolite.

A diluent material introduced by conduit 18 is combined with the ether rich effluent obtained as hereinbefore discussed before contact of the mixture is made with the HZSM-5 crystalline zeolite catalyst under heat generating or exothermic reaction conditions controlled to restrict the temperature increase between the reactor inlet and reactor outlet not to exceed about 111° C. (200° F.) and preferably not to exceed about 83° C. (150° F.). The conversion of the ether rich effluent by the HZSM-5 catalyst is highly exothermic as discussed above and controlled within desired limits by use of gasiform heat dissipating diluent material. During this highly exothermic operation the ether rich effluent or equilibrium mixture comprising dimethyl ether, methanol and water is controlled to effect the conversion thereof to gasoline boiling range components comprising aromatic and isoparaffins. The aromatic components comprising benzene, toluene and xylene are preferred components over the higher boiling durene aromatic material and efforts are made (e.g., reactant partial pressure, and reactant plug flow operation) to promote this end.

The product effluent of the HZSM-5 reaction zone 16 is passed through one or more cooling steps to reduce the temperature to a desire low temperature. In the specific arrangement of the figure the effluent is passed by conduit 20 to heat exchanger 22 wherein the effluent temperature is reduced to about 94° C. (200° F.) by indirect heat exchange with diluent material removed therefrom by conduit 18. The diluent will be at a temperature of about 315°–343° C. (600°–650° F.) The partially cooled effluent is removed from heat exchanger 22 and passed by conduit 24 to cooling water and/or air heat exchanger 26 wherein a further cooling of the effluent to about 38° C. (100° F.) is accomplished. Some of the effluent is passed via conduit 21 to heat exchangers 13, 11, and 8 to superheat, vaporize, and preheat, respectively, the methanol feed. The effluent from exchanger 8 is cooled in exchanger 26 and combined with cooled effluent from reactor conduit 20 and passed into separator 28, where liquid hydrocarbon, liquid water and gaseous material are separated. In the arrangement of the drawing, most of the gaseous effluent is then passed by conduit 30 to heat exchanger 22 where it is again passed in indirect heat exchange with reactor effluent and finally heater 38 before entering reactor 16. Water product is removed from separator 28 via conduit 34 for further treatment. Liquid hydrocarbon product is removed from separator 28 via conduit 32 and is sent to a product recovery section (not shown). Of course many other heat exchange arrangements may be provided for reducing the reactor effluent temperature from about 426° C. (800° F.) to about 38° C. (100 degrees F.) before passage to separator 28. Separator 28 is maintained at a temperature of about 38° C. (100° F.) and a pressure of about 1540 kPa (220 psig). In the separator a rough cut is made between gasiform diluent materials, desired aromatic and isoparaffin product and water. Water is withdrawn by conduit 34. A gasiform product material lower boiling than desired gasoline boiling range constituents is withdrawn by conduit 30 and passed to a compressor 36. A plurality of parallel arranged gas compressors may be used for this purpose. The gasiform material is compressed by compressor 36 to a pressure of about 2310 kPa (330 psig) before passage to exchanger 22. Excess gas is removed via conduit 39 and sent to product recovery.

The conversion of methanol or methanol equivalents is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 20:1 to 200:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constraint Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica:alumina ratio is correctly determined.

Preferred zeolites which have the specified values of Constraint Index and silica:alumina ratio include zeolites ZSM-5, ZSM-11, ZSM-12, ZSM-35, and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations they may be quite inactive possibly because the intracrystalline free space is occupied by the organic cations from the forming solution. The zeolite may be activated by heating in an inert atmosphere to remove the organic cations e.g.

by heating at over 500 degrees C. for 1 hour or more. The hydrogen form can then be obtained by base exchange with ammonium salts followed by calcination e.g. at 500 degrees C. in air. Other cations e.g. metal cations can be introduced by conventional base exchange techniques.

Specific Embodiments

In the conventional MTG process as practiced in the art heretofore, cycle average gasoline yields generally run about 80 to 85%. Typical cycle lengths are between 20 and 50 days before methanol breakthrough at 99.9% conversion occurs. Of course, virtually every process parameter can effect yield and cycle life, at least negatively, but by and large the aforenoted upper limits to yield and cycle length have resisted research efforts to practically increase them. In terms of methanol WHSV based on catalyst, current practice is to conduct the process at a nearly constant WHSV between 1 and 3, although the process can operate at weight hourly space velocity between 20 and 0.1 based on active catalyst weight.

Up to the moment of the discovery embodied in the present invention, while it was known that increasing methanol WHSV would instantaneously increase gasoline yield, it had been documented that a true overall cycle process advantage, as in enhanced cycle average yield, was not produced. At higher methanol WHSV the catalyst ages more. Therefore, if yields at high and moderate methanol WHSV are studied in terms of methanol processed per pound of catalyst, yields are equivalent. Documentation for this understanding of workers in the MTG field is presented in FIG. 2 which compares yields of 11 RVP gasoline on a weight percent of hydrocarbon (HC) basis at 2.3 and 1.6 WHSV.

Figure 2:
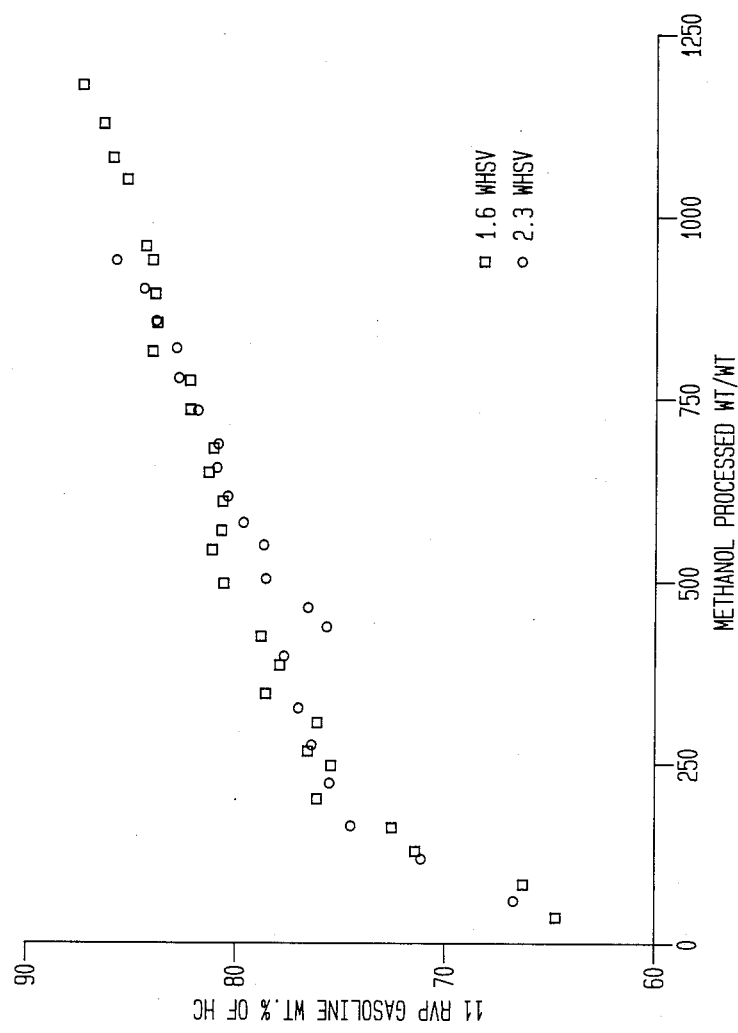
FIGS. 2 and 3 present methanol WHSV values compared against the resulting 11 RVP gasoline yields in a fixed bed MTG process.

It should be noted, as shown in FIG. 2, that at higher methanol WHSV the time to reach methanol breakthrough is shorter while the converse is true for lower WHSV. Hence, those skilled in the art believed that, as far as methanol WHSV is concerned, what may be achieved in instantaneous higher yield at higher methanol (WHSV) is effectively compromised by catalyst aging and shortened cycle length.

In the present invention it has been discovered that when methanol WHSV to the conversion reactor is programmed or varied improved cycle average yields of gasoline are recovered. Programming or varying the methanol WHSV means operating the MTG process at an initial or start-up WHSV to the conversion reactor that is high, i.e., above average according to the typical MTG process operation. However, the initial WHSV must be below the "methanol breakthrough" threshold which is conventionally about 99 to 99.9% methanol conversion. Preferably, the initial WHSV is not in excess of that space velocity at which methanol is quantitatively converted. From an initial high WHSV the programmed or variable methanol WHSV in MTG process is reduced or lowered in a controlled manner so as to maintain the WHSV about as high possible, dictated by methanol breakthrough considerations. This may be done by essentially continuously decreasing WHSV from the initial high value or decreasing WHSV in a staged or stepwise manner. The controlled drop-off in methanol WHSV continues in this manner, basically tracking that WHSV that approaches "methanol breakthrough" until, usually at a methanol WHSV significantly below the average WHSV employed in typical MTG operations, the cycle is terminated. The cycle is terminated when it is no longer operationally or economically feasible to continue to lower the WHSV to avoid methanol breakthrough.

In the operation of the present invention, where a typical average methanol WHSV to the conversion MTG reactor is between 1 and 3, a programmed WHSV would have an initial value of 10 and a terminal value of 0.1, but preferably the value under typical conditions for a commercial MTG process would be between an initial value of 5 and a terminal or end of cycle value of 0.5.

Figure 3:
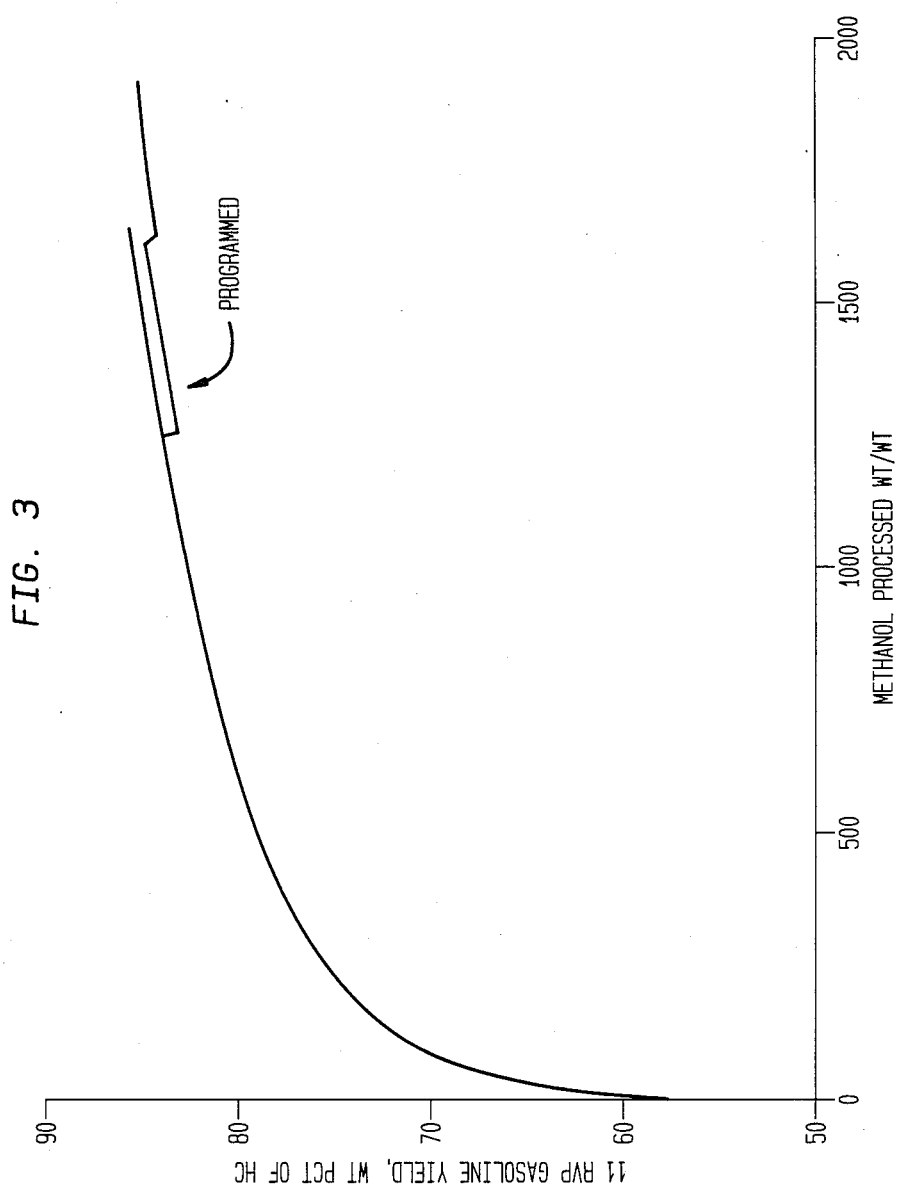

Referring to FIG. 3, based on the gasoline yield dependence on methanol processed per unit of catalyst, the improvement in cycle average gasoline yield expected from space velocity programming is shown for fresh catalyst. The methanol space velocity programming sequence involved operation at 1.8 methanol WHSV for 60% of the cycle, operation at 1.44 methanol WHSV for 20% of the cycle and operation at 1.2 methanol WHSV for the remaining 20% of the cycle. The cycle average methanol WHSV is the same as that for the non-programmed case. As can be seen from FIG. 3, gasoline yield was the same in both cases on a methanol processed basis until the methanol WHSV programming was implemented. Note also that the instantaneous gasoline yield dropped at the instant the programming was implemented. Nevertheless, the cycle average gasoline yield for the methanol WHSV programmed case was 80.5 wt % vs 80.0 wt % for the non-programmed case. In each case the average methanol WHSV was 1.6. Data for FIG. 3 are as follows:

| DATA BASE FOR FIG. 3 | | | |
| --- | --- | --- | --- |
| MEOH WHSV = | | | 1.6 |
| CYCLE LENGTH = | | | 42.6 DAYS |
| AVG 11 RVP GASOLINE YIELD | | | 80.0 WT PCT |
| WHSV PROGRAMMING | | | |
| AVG MEOH WHSV = | | | 1.6 |
| CALC CYCLE LENGTH = | | | 48 DAYS |
| CALC AVG 11 RVP GASO YIELD = | | | 80.5 WT PCT |
| STAGE | 1 | 2 | 3 |
| WHSV | 1.8 | 1.44 | 1.2 |
| CYCLE SPLIT | 0.6 | 0.2 | 0.2 |

It should be noted that the cycle length to methanol breakthrough is 42.6 days in the non-programmed case and greater than 48 days for the programmed case. In the present invention, then, methanol WHSV programming is also beneficial with respect to catalyst life. While not wishing to be held to theoretical considerations the current understanding of the demonstrated benefits of methanol WHSV programming derives from the following:

It is known that methanol conversion catalyst is permanently deactivated by steam. Higher temperatures accelerate the deactivation at the same steam partial pressure. In an adiabatic MTG reactor, the outlet temperature is greater than the inlet temperature. This results in catalyst toward the reactor outlet being more permanently deactivated than that toward the inlet. One factor affecting the width of the MTG reaction zone is the methanol WHSV. Increasing the methanol WHSV broadens the reaction zone and reduces the extent of permanent deactivation of the catalyst located toward the front of the catalyst bed. As the reaction zone moves toward the reactor outlet as the catalyst ages in a cycle, methanol WHSV programming tends to preserve the front of the catalyst bed. This section will be increasingly relied upon to carry the conversion process as the catalyst ages. In addition, as methanol WHSV programming operates at lower than cycle average WHSV toward the end of a cycle, the more deactivated catalyst toward the reactor outlet is better able to complete the methanol conversion than it would have been at the constant higher methanol WHSV in the non-programmed situation.

In the following examples the advantages of methanol WHSV programming are further documented.

EXAMPLE I

A fixed bed MTG process was operated using a conventional dehydration reactor followed by a ZSM-5 conversion reactor. Conditions included 83 wt % methanol feed, 2100 kPa (300 psig), 9/1 recycle ratio, 360° C. (680° F.) conversion reactor inlet temperature, and fifty days on-stream at a high and low methanol WHSV. Results are presented in Table I.

TABLE I

| Time On-Stream Days | 47 | 48 | 49 | 50 |
|---|---|---|---|---|
| MeOH WHSV | 1.6 | 1.6 | 0.8 | 0.8 |
| MeOH Conversion, % | 99.92 | 99.88 | 100 | 100 |
| 11 RVP Gasoline Yield, Wt % | 86.3 | 87.7 | 85.8 | 85.4 |
| 11 RVP Gasoline Octane, R + O | 92.8 | 92.7 | 93.0 | 92.8 |

These data show that decreasing methanol WHSV after methanol breakthrough will cause the methanol conversion to improve. Note that gasoline yield decreases and gasoline octane increases upon decreasing the methanol WHSV. The cycle average gasoline yield calculated for the data partially shown in Table I demonstrate the principle of methanol WHSV programming in that the average gasoline yield is higher for the data up to 50 days on stream than it is for the data up to 48 days on stream; the latter corresponds to methanol breakthrough at 1.6 methanol WHSV. Most advantageously, the methanol WHSV programming process for MTG leads as well to improved octane rating.

EXAMPLE II

Fixed bed MTG processes were operated using a conventional dehydration reactor followed by a ZSM-5 conversion reactor under the following identical conditions except for methanol WHSV:

| Feedstock | 83% methanol |
|---|---|
| Recycle ratio | 9/1 |
| Pressure | 2100 kPa |
| Inlet Temp. | 360° C. |

The results were as follows:

|  | IIa | IIb |
|---|---|---|
| MeOH WHSV | 1.6 | 1.6 → 0.8 |
| Cycle Length, days | 48 | 50* |
| Cycle Avg. Gaso. Yield, Wt % HC | 83.40 | 83.46* |
| Cycle Avg. Gaso. Octane, R + O | 93.4 | 93.4* |

*Cycle not completed at this space velocity.

In experiment IIa, conventional or non-programmed WHSV process, methanol breakthrough occurred at 48 days at a space velocity of about 1.6. However, in experiment IIb, when methanol WHSV was programmed from an initial value of 1.6, the experiment was terminated without methanol breakthrough after 50 days at a terminal WHSV of 0.8. The gasoline yield was clearly higher, cycle life longer, and, importantly, there was no deterioration in octane value.

Thus, methanol WHSV programming from high values at the start of the cycle to low values at the end of the cycle is seen to result in improved cycle average gasoline yield, and is also directly beneficial to catalyst life. The net effect of this improved MTG process is a more economically attractive MTG process.

Having thus generally described the process of the present invention and discussed specific embodiments in support thereof, it is to be understood that no undue restrictions as to the scope of the present invention are to be imposed by reason thereof.

What is claimed is:

1. In a process for converting at least 99.9% of $C_1-C_4$ oxygenates to primarily $C_5+$ gasoline boiling range hydrocarbons with a crystalline zeolite conversion catalyst, the improvement which comprises,
   selectively programming a feed weight hourly space velocity to a fixed bed catalytic conversion reactor during a process cycle so as to increase cycle average gasoline yield and increase useful life of the conversion catalyst.

2. The process of claim 1, wherein said programming comprises adjusting the feed weight hourly space velocity to the conversion reactor from high values at a start of the cycle to low values at an end of the cycle.

3. The process of claim 1, wherein the feed weight hourly space velocity is initially higher than an average feed weight hourly space velocity during the cycle.

4. A cyclic process for converting at least 99.9% of lower aliphatic oxygenated hydrocarbon feedstock to primarily $C_5+$ aromatics-rich gasoline range hydrocarbons comprising the step of:
   (a) contacting the feedstock with a fixed bed of acid shape selective medium pore zeolite conversion catalyst particles at elevated temperature under conversion conditions;
   (b) maintaining feedstock initial feed rate at high weight hourly space velocity in the presence of fresh acid catalyst having high acid activity;
   (c) decreasing the feedstock feed rate space velocity with decreasing acid catalyst activity during cycle progression; and
   (d) interrupting feedstock conversion at a predetermined low catalyst activity for periodic catalyst regeneration to increase catalyst activity.

5. The process of claim 4 wherein the feedstock comprises methanol, dimethylether or mixture thereof;
   wherein the zeolite catalyst comprises an aluminosilicate having a silica to alumina ratio of at least about 12 and a constraint index of about 1 to 12;
   wherein the process temperature is maintained between about 300 and 450 degrees C; and
   wherein the cycle weight hourly space velocity is decreased from start of cycle to end of cycle.

6. The process of claim 5 wherein the average cycle length increases under essentially quantitative methanol conversion conditions and the active catalyst consists essentially of HZSM-5 having a silica to alumina ratio of about 20:1 to 100:1.

7. The process according to claim 4 wherein the feedstock initial feedrate is at a WHSV of between 10 and 1.1 with end of cycle WHSV of about 0.5 to 1.0.

8. The process of claim 4 wherein the feedstock initial feedrate WHSV is at a maximum value compatible with an essentially quantitative conversion of said feedstock.

9. The process of claim 4 wherein the feedstock initial feedrate WHSV is reduced during the cycle by an amount just sufficient to maintain an essentially quantitative conversion of said feedstock, whereby the average cycle yield is enhanced and catalyst useful life extended.

10. The process of claim 9 wherein the feedstock feedrate WHSV is reduced continuously.

11. The process of claim 9 wherein the feedstock feedrate WHSV is reduced stepwise in stages.

12. In the fixed bed adiabatic process for converting at least 99.9% of lower aliphatic oxygenated hydrocarbons feedstock to primarily $C_5+$ aromatic-rich gasoline range hydrocarbons by dehydrating the lower aliphatic oxygenated hydrocarbons to form a dehydration product comprising dialkylether, contacting the dehydration product with a zeolite conversion catalyst under conversion conditions in a fixed bed adiabatic conversion zone at elevated temperature and essentially uniform cycle weight hourly space velocity for the feedstock feedrate and regenerating spent catalyst, the improvement which comprises;

charging said dehydration product to said conversion zone at a maximum feedrate space velocity compatible with at least 99.9% conversion of said feedstock, reducing space velocity during the cycle by an amount just sufficient to maintain at least 99.9% conversion of said feedstock, whereby the average cycle yield is enhanced and catalyst useful life extended.

13. The process of claim 12 wherein the dehydration product initial feedrate space velocity is reduced during the cycle by an amount just sufficient to maintain the conversion of said dehydration product at not less than 99.9%.

14. The process of claim 12 wherein said dehydration product WHSV is reduced continuously.

15. The process of claim 12 wherein said dehydration product space velocity is reduced stepwise in stages.

16. The process of claim 12 wherein the feedstock comprises methanol, dimethylether or mixtures thereof; wherein the zeolite catalyst comprises an aluminosilicate having a silica to alumina ratio of at least about 12 and a constraint index of about 1 to 12; wherein the process temperature is maintained between about, 300° and 450° C.

17. The process of claim 12 wherein the catalyst consists essentially of ZSM-5.

* * * * *